United States Patent [19]
Finke et al.

[11] 3,950,413
[45] Apr. 13, 1976

[54] PROCESS FOR THE PREPARATION OF PHOSPHONIC ACID DIHALIDES

[75] Inventors: Manfred Finke, Fischbach, Taunus; Hans-Jerg Kleiner, Bad Soden, Taunus, both of Germany

[73] Assignee: Hoechst Aktiengesellschaft, Frankfurt am Main, Germany

[22] Filed: May 23, 1974

[21] Appl. No.: 472,801

Related U.S. Application Data

[63] Continuation of Ser. No. 299,850, Oct. 24, 1972, abandoned.

[30] Foreign Application Priority Data
Oct. 26, 1971 Germany............................ 2153149
Aug. 26, 1972 Germany............................ 2241993

[52] U.S. Cl. .................. 260/543 P; 260/465 G
[51] Int. Cl.² ................................ C07R 9/42
[58] Field of Search................. 260/543 P

[56] References Cited
UNITED STATES PATENTS
2,847,469  8/1958  Dawson et al.................. 260/543 P
2,929,843  3/1960  Dawson et al.................. 260/543 P
3,179,696  4/1965  Brown et al..................... 260/543 P
3,200,145  8/1965  Lutz et al. ...................... 260/543 P FOREIGN PATENTS OR APPLICATIONS
1,020,019  11/1957  Germany......................... 260/543 P

*Primary Examiner*—James A. Patten
*Attorney, Agent, or Firm*—Henry W. Koster

[57] ABSTRACT

A process for the preparation of phosphonic acid dihalides of the formula

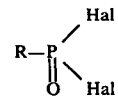

in which R is α, β-unsaturated alkyl, α, β-unsaturated alkyl, phenyl or benzyl and may be further substituted, which comprises reacting corresponding phosphonic or pyrophosphonic acids or their functional derivatives with acid halides of the formula $(CO)_nHal_2$ where $n$ is 1 or 2.

3 Claims, No Drawings

PROCESS FOR THE PREPARATION OF PHOSPHONIC ACID DIHALIDES

This is a continuation of application Ser. No. 299,850, filed Oct. 24, 1972, now abandoned.

The present invention relates to a process for the preparation of phosphonic acid dihalides.

It is known to react phosphonic acid dialkyl esters with acid chlorides such as $PCl_5$, $SOCl_2$ and $(COCl)_2$ to obtain the corresponding ester chlorides (Houben-Weyl, vol. 12/1 (1963), page 415).

Phosphonic acid dichlorides are obtained with $PCl_5$ or $PCl_3 + Cl_2$ only at temperatures of more than 100°C (loc. cit., page 388). However, in this process considerable difficulties are encountered in the separation of the process product from the $POCl_3$ formed as by-product.

It is further known to react short-chained alkane phosphonic acid dialkyl esters with gaseous thionyl chloride at temperatures of 130°–150°C to give the dichlorides (U.S. Pat. No. 2,847,469). Owing to the corrosive effect of the $SOCl_2$ or its secondary product $SO_2$ this process puts a great strain on the material of the apparatus.

The reaction of methanephosphonic acid di-isopropyl ester with phosgene at temperatures of from 100°–200°C and a pressure of 25 atmospheres gage has been described; however, the yield is only 48.5 % (U.S. Pat. No. 3,179,696). As is stated in the description of that patent, the reaction cannot be carried out at temperatures of less than 100°C.

The present invention provides a process for the preparation of phosphonic acid dihalides of the formula

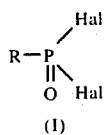

(I)

in which R an $\alpha,\beta$-unsaturated alkenyl having 2 to 18 carbon atoms, $\alpha,\beta$-unsaturated cycloalkenyl having 3 to 10, preferably 5–6 carbon atoms, phenyl or benzyl wherein R may be substituted by chlorine, bromine, lower alkyl, lower alkoxy, cyano or trifluoromethyl, and hal is halogen, preferably chlorine or bromine, which comprises reacting correspondingly substituted phosphonic or pyrophosphonic acids of the formulae

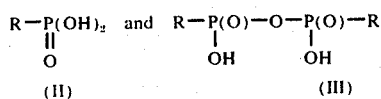

their monothio-analogs or their functional derivatives with acid halides of the formula

where $n$ is the 1 or 2, preferably with phosgene. Among the monothio-analogs and functional derivatives of the compounds of formulae II and III are correspondingly substituted thiophosphonic acid ester, phosphonic acid semiesters, diesters and salts especially alkali or ammonium salts, phosphonic acid ester halides, anhydrides, pyrophosphonic acid esters and semiesters as well as the monothio-analogs of these derivatives.

Among the phosphonic acid diesters are preferred those in which $R_1 = R_2$. The pyrophosphonic acid esters, phosphonic acid ester halides or phosphonic anhydrides mentioned occur, optionally also as intermediary products, in the conversion of the above phosphonic acid diesters with the acid halides and are applicable accordingly in the same way as initial materials.

Radicals of the formula R which are unsubstituted or substituted once are preferred. Examples for R are: vinyl, 1-methylvinyl, 1-propenyl, 2-chloro-vinyl, 2,2-dichloro-vinyl, 1-butenyl, 1-isobutenyl, 1-hexenyl, 1-hexadecenyl, cyclopropenyl-(1), cyclobutenyl-(1), cyclo-octenyl-(1); 2-, 3-or 4-chloro or bromo-phenyl, 4-cyano-phenyl, 2-, 3- or 4-trifluoro-methyl-phenyl, 4-methoxyphenyl, 4-ethoxy-phenyl, 2-, 3- or 4-methyl- or ethyl-phenyl, 2,4- or 3,4-dichloro-phenyl; 2-, 3-, 4- or $\alpha$-chloro-benzyl.

Esters and semi- esters of the phosphonic and pyrophosphonic acids are preferably those which as ester groups have alkoxy or haloalkoxy with 1 to 12 carbon atoms, in particular methoxy, ethoxy or $\beta$-chloroethoxy.

As starting products the following compounds are named for example:

vinyl phosphonic acid dimethyl ester, -ethyl ester, -n-propyl ester, -n-butyl ester, vinyl phosphonic acid-bis-2-chloro-ethyl ester, 1-methyl-vinyl-phosphonic acid dimethyl ester, cyclo hexene-1-yl-phosphonic acid dimethyl ester, benzylphosphonic acid dimethyl ester or diethyl ester, phenyl phosphonic acid dimethyl ester, or diethyl ester, 4-chloro-phenyl phosphonic acid dimethyl ester and also the corresponding ester chlorides, pyrophosphonic acid esters and phosphonic anhydrides.

Cyclohexene-1-phosphonic acid, phenyl-phosphonic acid, 4-methyl-phenyl-phosphonic acid, 4-chloro-phenyl-phosphonic acid, benzyl-phosphonic acid, phenyl-phosphonic acid monoethyl ester, benzyl-phosphonic acid mono-propyl ester, disodium salt of phenyl-phosphonic acid, mono-sodium salt of benzyl phosphonic acid, sodium salt of phenyl-phosphonic acid monoethyl ester.

The starting products mentioned can be prepared easily by known processes (cf. Houben-Weyl, 4th edition, volume 12/1, pages 415, 610, 612).

Suitable inert solvents are, for example, trichloroethane, tetrachloroethane, trichloroethylene, chlorobenzene, dichlorobenzene, diphenylmethane, chloronaphthalene or the end product, the latter being preferred.

As acid halides of formula III those are preferred in which hal is chlorine or bromine, i.e. phosgene, oxalyl chloride, bromo-phosgene and oxalyl bromide, preferably phosgene.

The process is carried out preferably at temperatures of between +65° and 200°C. Higher temperatures are also possible but offer no advantage. Especially preferred are reaction temperatures in the range of from +90° to +160°C.

The reaction may be carried out under pressure, for example at up to 10 atmospheres gage or, if there is no intermediate pressure release, also with the higher pressures arising from the formation of $CO_2$ (CO). Nevertheless working under atmospheric pressure is preferred.

The reaction time may vary depending on the temperature and apparatus used for the process. Generally it is in the range of from about 3 to 15 hours.

The reaction is advantageously carried out by introducing the acid halide into the phosphonic acid derivative, which is optionally dissolved in an inert solvent, and eliminating the waste products (alkyl halide and $CO_2$ or CO) in known manner, if possible already during the reaction, from the reaction zone, for example by distillation and/or fractional condensation.

When using salts of phosphonic or pyrophosphonic acids an inert solvent is necessary. It is, however, not necessary that the salts are dissolved in the solvent, it is sufficient for them to be suspended. It is expedient to use the end product as solvent or diluent. Phosgene is preferred as acid halide. The reaction is concluded, in general, within 2 to 30 hours depending on the conditions applied.

When using phosphonic or pyrophosphonic acid alkali metal salts as starting materials alkali metal halides occur as by-products. After the conclusion of the reaction they can be easily separated, for example by filtration. The use of phosphonic acid salts lessens or prevents the otherwise inherent formation of hydrogen halide.

A vigorous mixing is advantageous, particularly if gaseous acid halides such as phosgene are used. After the completion of the reaction the reaction product is isolated by distillation.

The use of a polymerisation inhibitor such as hydroquinone is advantageous for R = alkylene, especially for R = vinyl or chloro-vinyl, especially at higher reaction temperatures. An excess of acid halide over the stoichiometric quantity is not necessary but can be expedient for shortening the reaction time. The excess acid halide, which leaves the reaction zone with the waste gases, is preferably mixed with fresh initial product and expediently consumed in a column in counter current flow. The whole process can also be carried out continuously in known manner, in particular in a column or an equivalent apparatus. Unreacted acid halide can be recycled into the reaction after purification.

The phosphonic acid-halides prepared according to the invention are valuable intermediate products, for example for the preparation of plant protective agents, flame-proofing agents or growth regulators.

Owing to its simplicity the process has essential technical advantages, in particular due to the fact that the waste products are gases or can be distilled and may be separated easily from the reaction products. Above all, the $CO_2$ obtained can be purified easily in such a way that it can be released into the atmosphere without any damage to the environment.

The following Examples serve to illustrate the invention:

EXAMPLE 1

100 g of vinylphosphonic acid dimethyl ester were introduced into a glass flask, provided with stirrer, thermometer, reflux condenser and gas inlet tube. Phosgene was introduced at 100°–110°C, while stirring quickly for 6.5 hours. The mixture was distilled in vacuo.

100 g of vinylphosphonic acid dichloride were obtained corresponding to a yield of 94 percent of the theory.

EXAMPLE 2

100 g of vinylphosphonic acid diethyl ester were introduced into the apparatus described in Example 1 and phosgene was introduced at a temperature of 140°C for 9 hours while stirring quickly. At the end of the conversion the mixture was distilled in vacuo.

71 g of vinylphosphonic acid dichloride were obtained corresponding to a yield of 80 percent of the theory.

EXAMPLE 3

85 g of vinylphosphonic acid-di-n-butyl ester were introduced into the apparatus described in Example 1. Phosgene was introduced at a temperature of from 150°–160°C while stirring vigorously for 8 hours. The n-butyl chloride formed was distilled off via a column. At the end of the reaction the mixture was distilled.

45 g of vinyl phosphonic acid dichloride were obtained corresponding to a yield of 80.5 percent of the theory.

EXAMPLE 4

75 g of 1-methylvinylphosphonic acid dimethyl ester were introduced into the apparatus described in Example 1. Phosgene was introduced at a temperature of from 100°–110°C while stirring vigorously for 7 hours. Subsequently the mixture was distilled.

62 g of 1-methyl vinylphosphonic acid dichloride were obtained, b.p. 40°C/0.03 mm Hg corresponding to a yield of 78 percent of the theory.

EXAMPLE 5

Phosgene was introduced into 100 g of cyclohexene-1-yl-phosphonic acid dimethyl ester, in the apparatus described in Example 1, while stirring vigorously for 7 hours at a temperature of 110°C. The mixture was subsequently distilled, 79 g of cyclohexene-1-yl-phosphonic acid dichloride were obtained b.p. 87°C/0.05 mm Hg corresponding to a yield of 75 percent of the theory.

EXAMPLE 6

78 g of vinylphosphonic acid ethyl ester chloride were filled into the apparatus described in Example 1. At a temperature of 140°C phosgene was introduced while stirring vigorously for 13 hours. The mixture was subsequently distilled.

63 g of vinyl phosphonic acid dichloride were obtained corresponding to a yield of 86 percent of the theory.

EXAMPLE 7

In 35 g of phenylphosphonic acid dimethyl ester phosgene was introduced in the apparatus described in Example 1 while stirring vigorously at a temperature of from 100°–110°C for 5 hours. The mixture was subsequently distilled.

33 g of phenylphosphonic acid dichloride were obtained, b.p. 70°–72°C/0.2 mm Hg corresponding to a yield of 90 percent of the theory.

EXAMPLE 8

Phosgene was introduced into 60 g of phenylphosphonic acid diethyl ester in the apparatus described in Example 1 at a temperature of 140°C while stirring vigorously for 7.5 hours. Subsequently the mixture was distilled.

39 g of phenylphosphonic acid dichloride were obtained corresponding to a yield of 71 percent of the theory.

EXAMPLE 9

90 g of p-chlorophenylphosphonic acid dimethyl ester were heated in the apparatus described in Example 1 at 110°C. At this temperature phosgene was introduced for 5.5 hours and subsequently the reaction mixture was distilled.

86 g of p-chlorophenylphosphonic acid dichloride were obtained, b.p. 91°–93°C.0.2 mm Hg corresponding to a yield of 92 percent of the theory.

EXAMPLE 10

116 g of benzylphosphonic acid dimethyl ester were filled into the apparatus described in Example 1 and heated to 100°–120°C. At this temperature phosgene was introduced while stirring vigorously for 6 hours. Subsequently, the mixture was distilled.

120 g of benzylphosphonic acid dichloride were obtained, b.p. 103°/0.3 mm Hg, m.p. 60° – 62°C. This corresponded to a yield of 99 percent of the theory.

EXAMPLE 11

Phosgene was introduced into a solution of 49 g of p-chlorophenylphosphonic anhydride in 50 g of p-chlorophenylphosphonic acid dichloride according to Example 1 at 100°–110°C for 6 hours. The residue was distilled under reduced pressure.

45 g of p-chlorophenylphosphonic acid dichloride were obtained, b.p. 102°C under 0.3 mm Hg corresponding to a yield of 78 percent of the theory.

EXAMPLE 12

95 g of oxalyl chloride were added dropwise within 3 hours at a temperature of 110°–115°C to 49 g of phenylphosphonic acid dimethyl ester in the apparatus according to Example 1. The mixture was then stirred for one hour at 115°C. Subsequently the mixture was distilled at reduced pressure.

43 g of phenylphosphonic acid dichloride were obtained, b.p. 116°C under 3 mm Hg, corresponding to a yield of 84 percent of the theory.

EXAMPLE 13

Phosgene was introduced into a mixture of 200 g of phenylphosphonic acid and 300 ml of chlorobenzene at a temperature of 130°C while stirring vigorously for 10 hours. Subsequently nitrogen was blown through the reaction solution to remove the excess phosgene and the solution was distilled under reduced pressure.

186 g of phenylphosphonic acid dichloride were obtained, b.p. 88°C under 0.6 mm Hg, corresponding to a yield of 75 percent of the theory.

EXAMPLE 14

250 g of benzylphosphonic acid were heated at 180°C, and phosgene was introduced for 4 hours. Subsequently the reaction mixture was degassed at 100°C in vacuo. Then the mixture was distilled.

293 g of benzylphosphonic acid dichloride were obtained, b.p. 103°C under 0.3 mm Hg; m.p. 60°–62°C, corresponding to a yield of 100 percent of the theory.

EXAMPLE 15

90 g of sodium salt of phenylphosphonic acid mono ethyl ester were suspended in 500 ml of chloro-benzene and phosgene was introduced at 120°C for 25 hours. Subsequently nitrogen was blown through at room temperature, the reaction mixture was suction filtered from the precipitated sodium chloride, the chlorobenzene was distilled off in vacuo and the residue distilled at 0.5 mm of mercury.

70 g of phenylphosphonic acid dichloride were obtained, corresponding to a yield of 82.5 percent of the theory.

EXAMPLE 16

Into a mixture of 67 g of p-chlorophenylphosphonic acid and 20 g of p-chlorophenylphosphonic acid dichloride phosgene was introduced at a temperature of from 180°–190°C for 20 hours. After blowing through nitrogen to remove excess phosgene the mixture was distilled under reduced pressure. 66 g of p-chlorophenylphosphonic acid dichloride were obtained corresponding to a yield of 84 percent of the theory.

EXAMPLE 17

Into a mixture of 57 g of cyclohexene-1-phosphonic acid and 10 g of cyclohexene-1-phosphonic acid dichloride phosgene was introduced at a temperature of from 170°–180°C for 19 hours. At the end of the reaction, nitrogen was blown through the mixture to remove excess phosgene and subsequently the mixture was distilled under reduced pressure. 62 g of cyclohexene-1-phosphonic acid dichloride were obtained, b.p. 75°C under 0.3 mm Hg, corresponding to a yield of 89.5 percent of the theory.

What is claimed is:

1. A process for the preparation of phosphonic acid dihalides of the formula $$R-\underset{\underset{O}{\parallel}}{P}\diagup_{Hal}^{Hal}$$

in which R is $\alpha,\beta$-unsaturated alkenyl having 2 to 18 carbon atoms, $\alpha,\beta$-unsaturated cycloalkenyl having 3 to 10, preferably 5–6 carbon atoms, phenyl or benzyl wherein R may be substituted by chlorine, bromine, lower alkyl, lower alkoxy, cyano or trifluoromethyl, and Hal is chlorine or bromine, which comprises reacting, at atmospheric pressure, correspondingly substituted phosphonic or pyrophosphonic acids of the formulae $$R-\underset{\underset{O}{\parallel}}{P}(OH)_2 \quad \text{and} \quad R-\underset{OH}{P(O)}-O-\underset{OH}{P(O)}-R$$

(II) \qquad\qquad (III)

their monothio-analogs or their functional derivatives with acid halides of the formula $$(CO)_nHal_2$$

where $n$ is 1 or 2.

2. A process as claimed in claim 1 wherein R is vinyl.

3. A process for the preparation of phosphonic acid dihalides as recited in claim 1 wherein the temperature of the reaction is from 65° to 200°C.

* * * * *